(12) United States Patent
Galdi et al.

(10) Patent No.: US 6,645,474 B1
(45) Date of Patent: Nov. 11, 2003

(54) STABLE SELF-TANNING FOAMS CONTAINING SODIUM COCO-SULFATE

(75) Inventors: Angelike A Galdi, Westfield, NJ (US); Isabelle Hansenne, Westfield, NJ (US)

(73) Assignee: Societe l'Oreal S.A., Paris (FR)

( * ) Notice: Subject to any disclaimer, the term of this patent is extended or adjusted under 35 U.S.C. 154(b) by 0 days.

(21) Appl. No.: 10/310,862

(22) Filed: Dec. 6, 2002

(51) Int. Cl.[7] .............................. A61K 7/42; A61K 7/44; A61K 7/00
(52) U.S. Cl. ........................... 424/59; 424/60; 424/400; 424/401
(58) Field of Search ............................ 424/59, 60, 400, 424/401

(56) References Cited

U.S. PATENT DOCUMENTS 5,965,594 A * 10/1999 Schoenberg et al. ........ 514/389
6,231,837 B1 * 5/2001 Stroud et al. .................. 424/59

* cited by examiner

*Primary Examiner*—Shelley A. Dodson
(74) *Attorney, Agent, or Firm*—Burns, Doane, Swecker & Mathis, L.L.P.

(57) ABSTRACT

Homogeneous, stable artificial/sunless skin tanning foams comprise an effective skin tanning amount of at least one self-tanning agent, most notably dihydroxyacetone ("DHA"), and an effective foam quality-augmenting and visual and self-tanning agent stability-enhancing amount of the surfactant, sodium coco-sulfate.

12 Claims, No Drawings

STABLE SELF-TANNING FOAMS CONTAINING SODIUM COCO-SULFATE

BACKGROUND OF THE INVENTION

1. Technical Field of the Invention

The present invention relates to novel non-aerosol self- or artificial/sunless tanning foams that incorporate a judiciously selected surfactant, sodium coco-sulfate, which augments foam quality and which enhances both visual and self-tanning agent stability.

This invention also relates to a regime or regimen for the artificial/sunless tanning of human skin by topically applying thereon, for such period of time as required to elicit the desired self-tanning effect, a stable cosmetic/dermatological foaming composition comprising an artificial/sunless tanning agent, most notably dihydroxyacetone ("DHA"), and the surfactant sodium coco-sulfate, formulated into a topically applicable, cosmetically/dermatologically acceptable vehicle, diluent or carrier therefor.

2. Description of the Prior Art

It is known to this art that non-aerosol self-tanning foams are difficult and problematic to formulate because of the sensitivity of, for example DHA, to amine functional groups. Nonetheless, amine functions are present in almost all of the commercially available surfactants. And this is the reason there are but very few non-aerosol self-tanning foams available on the commercial market.

Indeed, one such commercially available non-aerosol self-tanning foam contains a DHA-compatible surfactant. To the contrary, however, visual stability issues (sedimentation) developed within 1–3 weeks after formulation at 5° C., 25° C., 37° C. and 45° C.

Oil-in-water stable emulsions (but not foams) are also known to this art which contain the self-tanning agent DHA in combination with a stabilizing amount of the sunscreen, octyl dimethyl PABA. Compare U.S. Pat. No. 4,434,154 to McShane. Cf. U.S. Pat. No. 3,177,120 to Black et al.; DE 19955375 A1.

SUMMARY OF THE INVENTION

Accordingly, a major object of the present invention is the provision of novel non-aerosol self- or artificial/sunless tanning foams that incorporate a particular surfactant to date never before included in self-tanning systems, such particular surfactant, sodium coco-sulfate, not only augmenting the foam quality while not degrading, for example the dihydroxyacetone, DHA, but also even enhancing the stability thereof.

This invention thus features formulating a judiciously selected surfactant, sodium coco-sulfate, which does not contain an amine functional group, into non-aerosol artificial/sunless tanning foams to enhance the quality thereof, as well as both visual and DHA stability.

Too, the present invention features a regime or regimen for the artificial/sunless tanning of human skin by topically applying thereon a homogeneous very good quality foam comprising an artificial/sunless tanning agent, characteristically DHA, and the surfactant sodium coco-sulfate, formulated into a topically applicable, cosmetically/ dermatologically acceptable vehicle, diluent or carrier therefor.

DETAILED DESCRIPTION OF BEST MODE AND SPECIFIC/PREFERRED EMBODIMENTS OF THE INVENTION

More particularly according to the present invention, novel non-aerosol self-tanning foams are hereby provided that include a surfactant, sodium coco-sulfate, which does not contain an amine function, which augments foam stability and which enhances both visual and DHA stability.

The DHA stability was especially good. Indeed, after 8 weeks, the DHA loss was determined to be <10% at room temperature (25° C.) and <30% at 45° C. (as measured via that USTM #132 technique referred to later herein).

Sodium coco-sulfate is the sodium salt of the sulfate ester of coconut alcohol that conforms generally to the formula:

$$ROSO_3Na$$

wherein R represents the alkyl groups derived from coconut oil. The technical name is sulfuric acid, monococoyl ester, sodium salt. Also, INCI name: sodium coco-sulfate; CAS No. 68955-19-1; EINECS No. 273-257-1.

Sodium coco-sulfate is an infrequently-used surfactant for personal cleansing products, but has never been incorporated into artificial/sunless tanning foams.

Too, sodium coco-sulfate behaves quite differently from the traditional surfactants, representative of which being sodium lauryl sulfate. The following data compare the general differences existing between the two surfactants.

| Property | Sodium Lauryl Sulfate | Sodium Coco-sulfate |
|---|---|---|
| Appearance | Liquid, typically 30% active | Anhydrous flake, typically 90% active |
| Solubility in water | Disperses readily | Requires heat to disperse |
| Foam properties | Excellent flash foam | Provides dense lather |
| Viscosity building | Requires a builder such as amide, betaine or amine oxide | Excellent. Does not require a builder. Often requires a hydrotrope to reduce viscosity |
| Conditioning | Not applicable. Needs added conditioner | Provides mild conditioning |

A preferred sodium coco-sulfate according to the present invention is that marketed by McIntyre Group Ltd. as MACKOL™ CAS-100F. It is said to be a special, naturally derived flaked form of sodium coconut oil fatty alcohol sulfate, developed for all natural shampoos and skin cleansing products. It is an easy-to-handle flowable flake, having a low free fatty alcohol content which is said to maximize formulating flexibility.

Its specifications and suggested applications are reported as follows:

SPECIFICATIONS:

| | |
|---|---|
| Appearance: | Cream colored flakes |
| Actives (MW306) %: | 90.0 Minimum |
| Sodium Sulfate %: | 2.0 Maximum |
| Sodium Chloride %: | 1.0 Maximum |
| Unsulfated Alcohol %: | 2.5 Maximum |
| pH (10% Aq.): | 9.0–12.0 |

APPLICATIONS:
Shampoos
Bath Products
Skin Cleansers
Liquid Dishwash

MACKOL™ CAS-100F is thus marketed as a 90% active granular product by weight, namely, as a unique, naturally derived, granular anionic surfactant for the formulation of "natural type" personal cleansing products.

The approximate composition of MACKOL™ CAS-100F is as follows:

| Component | Weight Percent | CAS No. | EINECS No. |
|---|---|---|---|
| Sodium Coco-Sulfate | 94 | 68955-19-1 | 273-257-21 |
| Sodium Chloride | 2 | 7647-14-5 | 231-598-3 |
| Sodium Sulfate | 2 | 7757-82-6 | 231-820-9 |
| Coco Alkyl Fatty Alcohol | 2 | 68425-37-6 | 270-351-4 |

Another specific sodium coco-sulfate according to this invention, albeit less preferred than MACKOL™ CAS-100F, is that anionic alkyl sulfate marketed as Sulfopon® HC Granulate by Henkel-Cognis; chain length distribution:

| | |
|---|---|
| $C_{12}$–$C_{14}$ (%) | 20–30 |
| $C_{16}$–$C_{18}$ (%) | 70–80. |

Sulfopon® HC Granulate is a recommended surfactant for the manufacture of hand cleaning pastes, especially for customers who encounter difficulties in terms of handling and processing of FAS pastes due to insufficient equipment.

These white granules are said to be (1) easy to handle, (2) high in active matter content, (3) nearly dustless, (4) a solid with excellent flowability, (5) easy to store over long periods, (6) not prone to hydrolysis, and (7) quickly soluble in warm water at 70° C.

The preferred chain length distribution of the sodium coco-sulfate ($C_{12}$–$C_{18}$ fatty alcohol sulfate, sodium salt) according to the invention is on the order of:

| | |
|---|---|
| $C_{12}$–$C_{14}$ (%) | 70–80 |
| $C_{16}$–$C_{18}$ (%) | 20–30. |

Such chain length distribution of the surfactant provides both optimal foam quality and stability of the self-tanning system, i.e., finished product homogeneous and foam quality very good.

It has also been determined that the optimal concentration of the sodium coco-sulfate in the subject non-aerosol self-tanning foams is on the order of 3%–4% by weight, more preferably on the order of 3% by weight (2.835% by weight active material). Those compositions containing 3% by weight of sodium coco-sulfate uniformly exhibit good foam quality as well as stability.

The subject artificial/sunless, or self-tanning cosmetic/dermatological compositions of this invention comprise an effective amount of at least one artificial/sunless tanning agent, notably dihydroxyacetone or DHA, for example on the order of 5% by weight.

To date, a wide variety of artificial tanning agents has been developed. Artificial tanners provide the highly sought-after tanning or darkening response once only available through harmful exposure to ultraviolet radiation. DHA, in particular, has been widely utilized in cosmetics to accomplish artificial tanning of the skin. Proteins of the epidermis have a very high concentration of arginine, lysine, and histidine and the reaction of skin with DHA to produce an artificial tan takes advantage of this fact. The tanning reaction proceeds through combination with free amino groups in skin proteins, and particularly by combination of DHA with the free guanido group in arginine.

Preferred among those artificial tanners which are useful in the compositions in the instant invention are those selected from the group comprising: allose, alpha hydroxy substituted ketones such as dihydroxyacetone, altrose, arabinose, erythrose, fructose, galactose, glucose, glyceraldehyde, indoles, lactose, mannose, reose, ribose, pentose, sucrose, tallose, xylose, and mixtures thereof.

Most preferred among those artificial/sunless tanners which are useful in the compositions of the present inventions is dihydroxyacetone. In this respect, it should be appreciated that DHA is not at all easy to formulate, is particularly sensitive and compositions comprised thereof tend to be quite unstable over time, (as DHA tolerates but few raw materials, e.g., carbomers). Thus, the stable formulations according to the invention are all the more unexpected and surprising.

In order to further illustrate the present invention and the advantages thereof, the following specific examples are given, it being understood that same are intended only as illustrative and in nowise limitative.

In said examples to follow, all parts and percentages are given by weight, unless otherwise indicated.

EXAMPLE 1

A skeleton formulation was developed, having the following composition:

| | |
|---|---|
| 12% | Surfactants[1] |
| 7% | Emollients/Solvents |
| 5% | DHA |
| 1.5% | Colorants |
| 1% | Preservatives |
| 0.3% | Fragrance |
| 0.1% | Cellulose Gum/Foam Stabilizer |

[1] The 12% surfactants was composed of 3% of the surfactant to be evaluated, 5% of isoceteth (non-ionic) and 4% of polysorbate (non-ionic).

EXAMPLES 2–6

The non-aerosol self-tanning foams set forth in the following Table I were formulated and evaluated in terms of foam aspects, visual and DHA stability, each containing 3% of the indicated surfactant and otherwise having the skeleton formulation reported in Example 1.

TABLE I

| Example | Surfactant Class | INCI Name | Trade Name/Supplier | Foam Aspect | Visual Stability[2] | DHA Stability[3] |
|---|---|---|---|---|---|---|
| 2 | Amphoteric: Betaine | Coco-Betaine | Dehyton AB 30 OR/Cognis | creamy foam | sediment evident at week 2 (5° C., 37° C.); week 8 (45° C.) | |
| 3 | Anionic: Monoalkyl Sulfosuccinate | Disodium PEG-12 Dimethicone Sulfosuccinate | Mackanate DC-50/McIntyre Group Ltd. | no foam | n/a | |

TABLE I-continued

| Example | Surfactant Class | INCI Name | Trade Name/Supplier | Foam Aspect | Visual Stability[2] | DHA Stability[3] |
|---|---|---|---|---|---|---|
| 4 | Anionic: Alkyl Sulfate | Sodium Coco-Sulfate | Mackol CAS 100 F/McIntyre Group Ltd. | creamy foam | stable at all exposures for 8 weeks | week 4 (25° C.): −4.2% week 8 (25° C.): −5.8% week 4 (45° C.): −17% week 8 (45° C.): −28.2% |
| 5 | Anionic: Alkyl Sulfate | Sodium Coco-Sulfate | Sulfopon HC Granulate/Henkel-Cognis | watery foam | n/a | |
| 6 | Non-Ionic: Alkyl Polyglucoside | Ecyl Ployglucoside | n/a | creamy foam | sediment evident at week 1 (25° C.); week 3 (5° C., 37° C., 45° C.) | |

[2]Visual stability was conducted for 8 weeks at exposures/temperatures of 5° C., 25° C., 37° C. and 45° C.
[3]DHA stability was determined via enzyme assay method (USTM #132). In this procedure, the hydrogenation of DHA to glycerol by GDH is coupled with the dehydrogenation of NADH and a decrease in its absorbance (measured at 365 nm). This absorbance change is directly proportional to the percentage (%) of DHA present in the sample, when all reaction ingredients other than sample or standard are in excess.

EXAMPLE 7

A 1,000g batch of a tinted foam composition and containing sodium coco-sulfate was formulated, having the composition set forth in the Table II which follows:

TABLE II

| Phase | Chemical Name | % wt/wt | Total g |
|---|---|---|---|
| A | isoceteth −20 | 5.0000% | 50.0000 |
| | dioctyl cyclohexane | 2.5000% | 25.0000 |
| | polysorbate 20 | 4.0000% | 40.0000 |
| | phenonip | 1.0000% | 10.0000 |
| | C12–15 alkyl lactate | 0.2500% | 2.5000 |
| B | glycerin | 2.5000% | 25.0000 |
| | propylene glycol | 2.0000% | 20.0000 |
| | di water | 47.3775% | 473.7750 |
| | sodium coco-sulfate | 3.0000% | 30.0000 |
| C1 | tocopherol/ soybean oil | 0.5000% | 5.0000 |
| | fragrance | 0.3000% | 3.0000 |
| C2 | hydroxypropyl methyl cellulose | 0.1000% | 1.0000 |
| D | DHA | 5.0000% | 50.0000 |
| | di water | 10.0000% | 100.0000 |
| E | di water | 12.9500% | 129.5000 |
| F | di water | 2.0000% | 20.0000 |
| | caramel | 1.5000% | 15.0000 |
| | FD & C Yellow No. 6 | 0.0200% | 0.2000 |
| | Red No. 33 | 0.0025% | 0.0250 |

This stable foam, pH=5.54 (24 hours), was prepared by introducing the Phases B1 and E into a main kettle and heated under propeller mixing to 40° C.–45° C.

Phase A was then combined into a side kettle and heated under moderate propeller mixing to 40° C.–45° C.

After the contents of both kettles attained a temperature of 40° C.–45° C. and were homogeneous, the contents of the side kettle (Phase A) were added to the main kettle. The propeller mixing was continued for 15 minutes.

Cooling then commenced. At 35° C.–40° C., Phase C1 was added, thoroughly mixed, and then Phase C2 was added and also thoroughly mixed therein. At 35° C., the Phase D pre-mix was added and next the Phase E pre-mix was added to the main kettle.

At 25° C. the mixing was discontinued and the contents of the main kettle were permitted to cool.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A homogeneous, stable artificial/sunless skin tanning foam cosmetic/dermatological composition comprising an effective skin tanning amount of at least one self-tanning agent and an effective foam quality-augmenting and visual and self-tanning agent stability-enhancing amount of the surfactant, sodium coco-sulfate.

2. The homogeneous, stable artificial/sunless skin tanning foam composition as defined by claim 1, said at least one self-tanning agent comprising dihydroxyacetone (DHA).

3. The homogeneous, stable artificial/sunless skin tanning foam composition as defined by claim 2, comprising from about 3% to 4% by weight of said sodium coco-sulfate surfactant.

4. The homogeneous, stable artificial/sunless skin tanning foam composition as defined by claim 3, comprising about 3% by weight of said sodium coco-sulfate surfactant.

5. The homogeneous, stable artificial/sunless skin tanning foam composition as defined by claim 2, comprising about 5% by weight of said DHA.

6. The homogeneous, stable artificial/sunless skin tanning foam composition as defined by claim 2, formulated into a topically applicable, cosmetically/dermatologically acceptable vehicle, diluent or carrier therefor.

7. The homogeneous, stable artificial/sunless skin tanning foam composition as defined by claim 6, exhibiting a DHA loss after 8 weeks of <10% at room temperature.

8. The homogeneous, stable artificial/sunless skin tanning foam composition as defined by claim 6, exhibiting a DHA loss after 8 weeks of <30% at 45° C.

9. The homogeneous, stable artificial/sunless skin tanning foam composition as defined by claim 2, said sodium coco-sulfate comprising $C_{12}$–$C_{14}$ and $C_{16}$–$C_{18}$ chain length fractions.

10. A topically applicable, homogeneous, stable artificial/sunless skin tanning foam cosmetic/dermatological composition comprising an effective skin tanning amount of at least one self-tanning agent and an effective foam quality-augmenting and visual and self-tanning agent stability-enhancing amount of the surfactant, sodium coco-sulfate, formulated into a topically applicable, cosmetically/dermatologically acceptable vehicle, diluent or carrier therefor.

11. A regime or regimen for the artificial/sunless tanning of human skin, comprising topically applying thereon, for such period of time as required to elicit the desired self-tanning effect, a homogeneous, stable artificial/sunless skin tanning foam cosmetic/dermatological composition comprising an effective skin tanning amount of at least one self-tanning agent and an effective foam quality-augmenting and visual and self-tanning agent stability-enhancing amount of the surfactant, sodium coco-sulfate.

12. The regime or regimen for the artificial/sunless tanning of human skin as defined by claim 11, said at least one self-tanning agent comprising dihydroxyacetone (DHA).

* * * * *